US00PP26674P2

(12) United States Plant Patent
Zlesak

(10) Patent No.: US PP26,674 P2
(45) Date of Patent: May 3, 2016

(54) ROSE PLANT NAMED 'GAYE HAMMOND'

(50) Latin Name: *Rosa hybrida*
Varietal Denomination: Gaye Hammond

(71) Applicant: David Charles Zlesak, St. Paul, MN (US)

(72) Inventor: David Charles Zlesak, St. Paul, MN (US)

( * ) Notice: Subject to any disclaimer, the term of this patent is extended or adjusted under 35 U.S.C. 154(b) by 52 days.

(21) Appl. No.: 14/121,794

(22) Filed: Oct. 20, 2014

(51) Int. Cl.
*A01H 5/02* (2006.01)

(52) U.S. Cl.
USPC ..... Plt./104

(58) Field of Classification Search
USPC ..... Plt./104
See application file for complete search history.

*Primary Examiner* — Anne Grunberg

(57) ABSTRACT

Shrub rose plant having an upright, well-branched, and generally rounded plant habit; very vigorous growth; double flowers typically borne one per short to medium length stem; petal color starts out yellow with peach highlights and matures to creamy-white; continuous flowering throughout the growing season; strong resistance to black spot and powdery mildew; very glossy medium to dark green foliage; prominent relatively straight prickles and ability to root and grow vigorously from softwood and semi-hardwood cuttings.

6 Drawing Sheets

Latin name of the plant claimed: *Rosa hybrida.*
Variety denomination: 'Gaye Hammond'.

BACKGROUND OF THE INVENTION

The primary objective of making the cross between the two yellow flowered parents leading to 'Gaye Hammond' was to produce a new yellow flowered rose cultivar having the compact and well-branched growth habit of the female parent and the black spot resistance and glossy foliage of the male parent. The pollination between the parents occurred in late spring 2007. Seedlings from the cross germinated during the winter of 2007/2008 and 'Gaye Hammond' was identified as a superior seedling and first asexually propagated in the late spring of 2008.

The present invention relates to a new and distinct variety of rose plant of the shrub commercial class designated 'Gaye Hammond' which was originated by David Zlesak by crossing 'Rise 'N Shine' (disclosed in U.S. Plant Pat. No. 4,231) and 'BAIine' (disclosed in U.S. Plant Pat. No. 16,659).

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Upright, well-branched, and generally rounded plant habit;
2. Very vigorous growth;
3. Double flowers typically borne one per short to medium length stem;
4. Petal color starts out yellow with peach highlights and matures to creamy-white;
5. Continuous flowering throughout the growing season;
6. Strong resistance to black spot and powdery mildew;
7. Very glossy medium to dark green foliage;
8. Prominent relatively straight prickles;

9. Ability to root and grow vigorously from softwood and semi-hardwood cuttings.

Asexual reproduction of this new variety by rooting softwood and semi-hardwood cuttings, as performed at St. Paul, Minn., shows that the foregoing and all other characteristics and distinctions come true to form and are established and transmitted through succeeding propagations.

Comparison with Parents

'Gaye Hammond' produces double flowers with yellow petals displaying peach highlights on the adaxial surface as they open. Plants are well-branched, are generally more upright than spreading in plant habit, and have glossy, disease resistant foliage. 'Gaye Hammond' differs from its female parent 'Rise 'N Shine', in that 'Gaye Hammond' has larger flowers and a larger overall plant size, the foliage is glossier and healthier, and the prickles are larger and more prominent. Additionally, 'Rise 'N Shine' has flowers that have more petals and the petals do not have peach colored highlights as they unfurl. 'Gaye Hammond' differs from the male parent, 'BAIine', in that 'BAIine' has a shorter plant size with less branching and double yellow flowers without peach highlights as the petals open. 'Gaye Hammond' shares a similar number of petals per flower, flower size, shape and size of prickles, and glossy healthy foliage with its male parent 'BAIine'. 'Gaye Hammond' and its female parent 'Rise 'N Shine' share having a very well-branched plant habit. All three genotypes have blooms that age to creamy-white. 'Gaye Hammond' and 'BAIine' have been reliably crown hardy in St. Paul, Minn. (United States Department of Agriculture cold hardiness zone 4), while plants of 'Rise 'N Shine' have died from winter injury in the same garden.

Comparison with Similar Variety

The rose variety with the greatest similarity to 'Gaye Hammond' is 'AROyqueli' (marketed under the name Gold Medal™; disclosed in U.S. Plant Pat. No. 5,177), a rose of the grandiflora commercial class. Both 'Gaye Hammond' and 'AROyqueli' have double yellow flowers with peach highlights on the adaxial petal surface and an upright plant habit. 'Gaye Hammond' has blooms that typically are slightly smaller, have less petals, and are produced in greater abundance than 'AROyqueli'. The foliage of 'Gaye Hammond' is also glossier and more disease resistant than 'AROyqueli'.

BRIEF DESCRIPTION OF THE DRAWINGS

The accompanying illustration shows typical specimens of the vegetative growth and flowers of this new variety in different stages of development, depicted in color as true as it is reasonably possible to make in a color illustration.

DETAILED BOTANICAL DESCRIPTION

Figure 1:
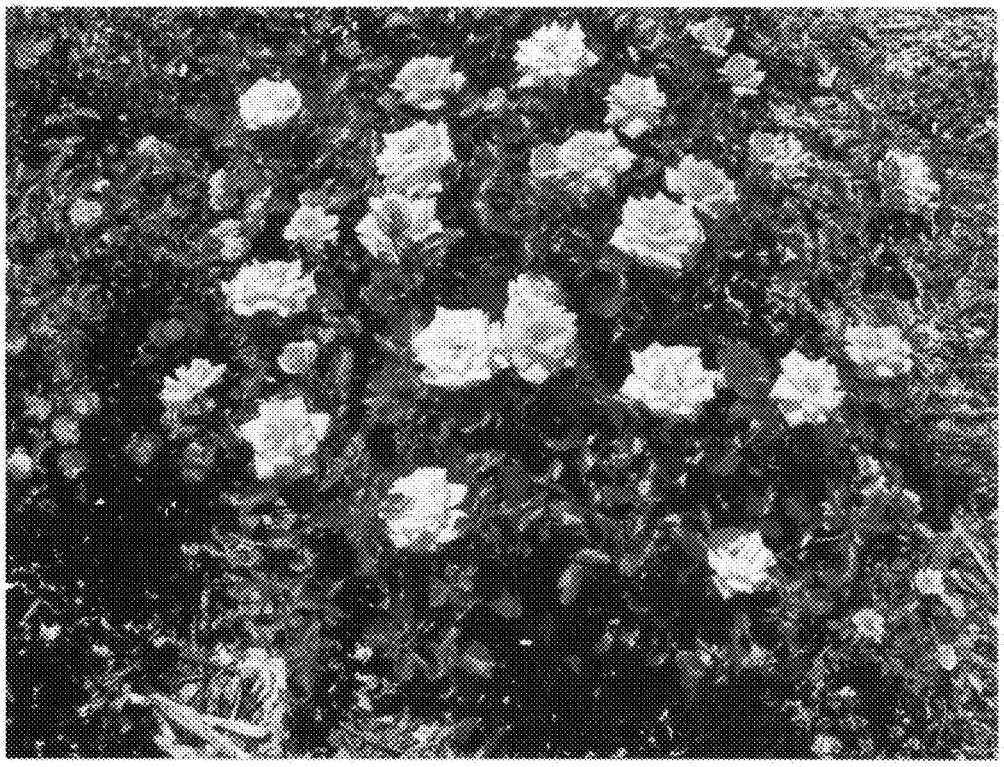
FIG. 1 illustrates a mature plant growing in a landscape during its first cycle of bloom in June.
Figure 2:
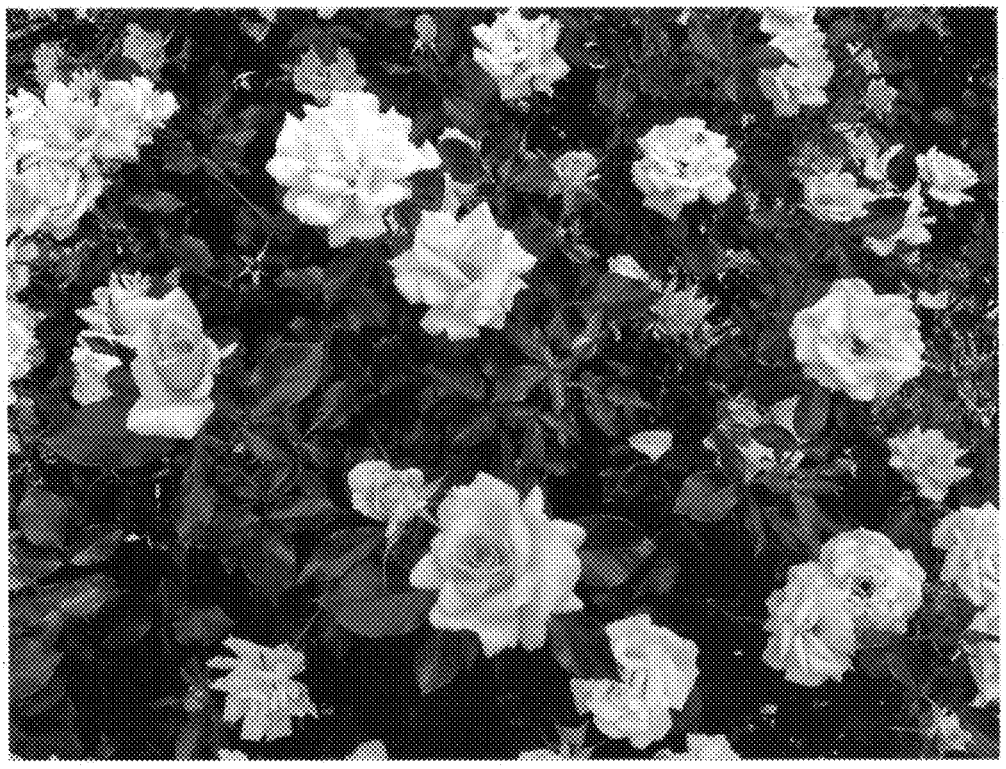
FIG. 2 illustrates a close up view of multiple flowers at different stages of opening.
Figure 3:
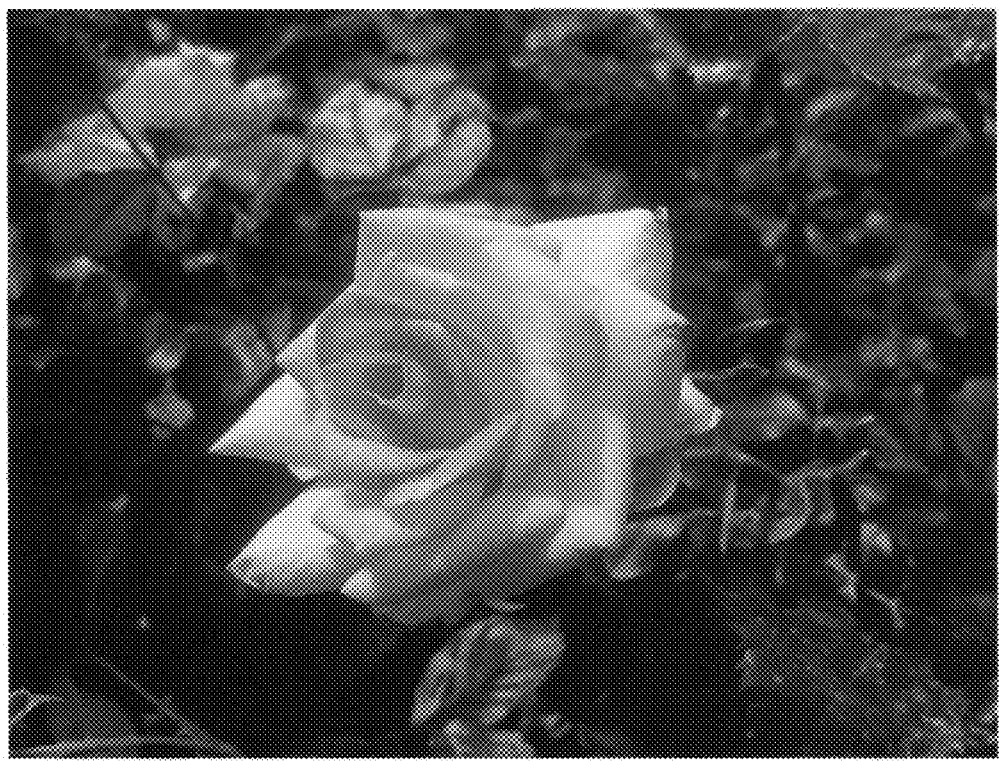
FIG. 3 illustrates a close up view of a flower that is partially opened.
Figure 4:
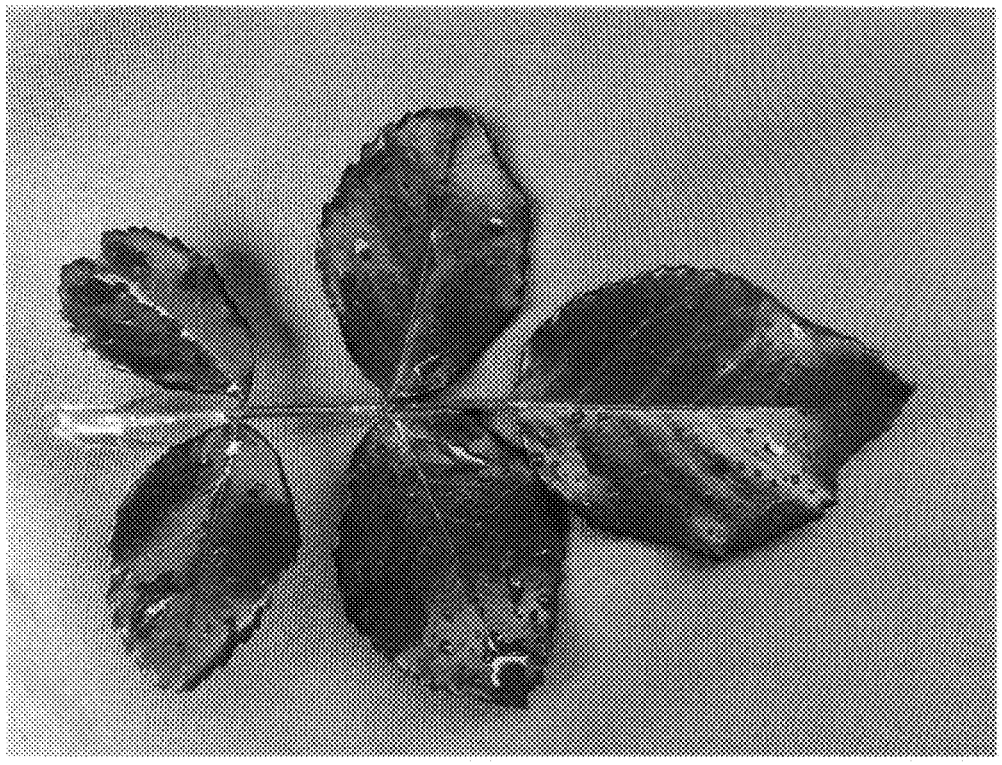
FIG. 4 illustrates a typical leaf.
Figure 5:
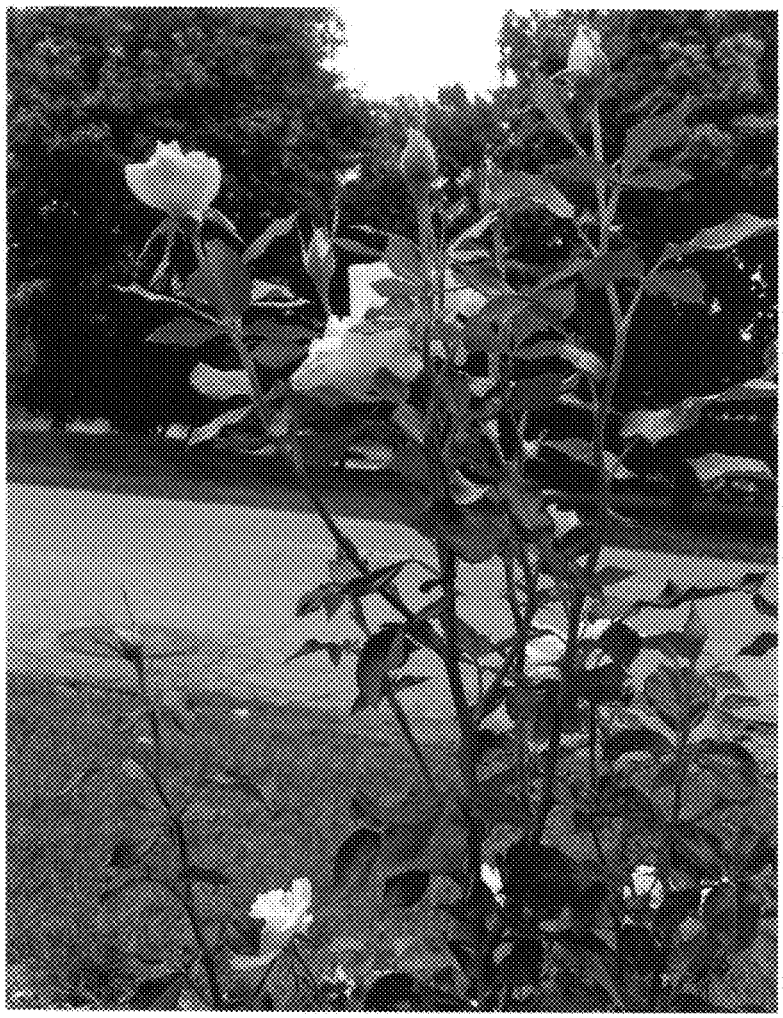
FIG. 5 illustrates the branching habit of a typical vigorous stem starting from the base of the plant and producing multiple secondary branches terminating in secondary flowers at a similar plane as the primary flower.
Figure 6:
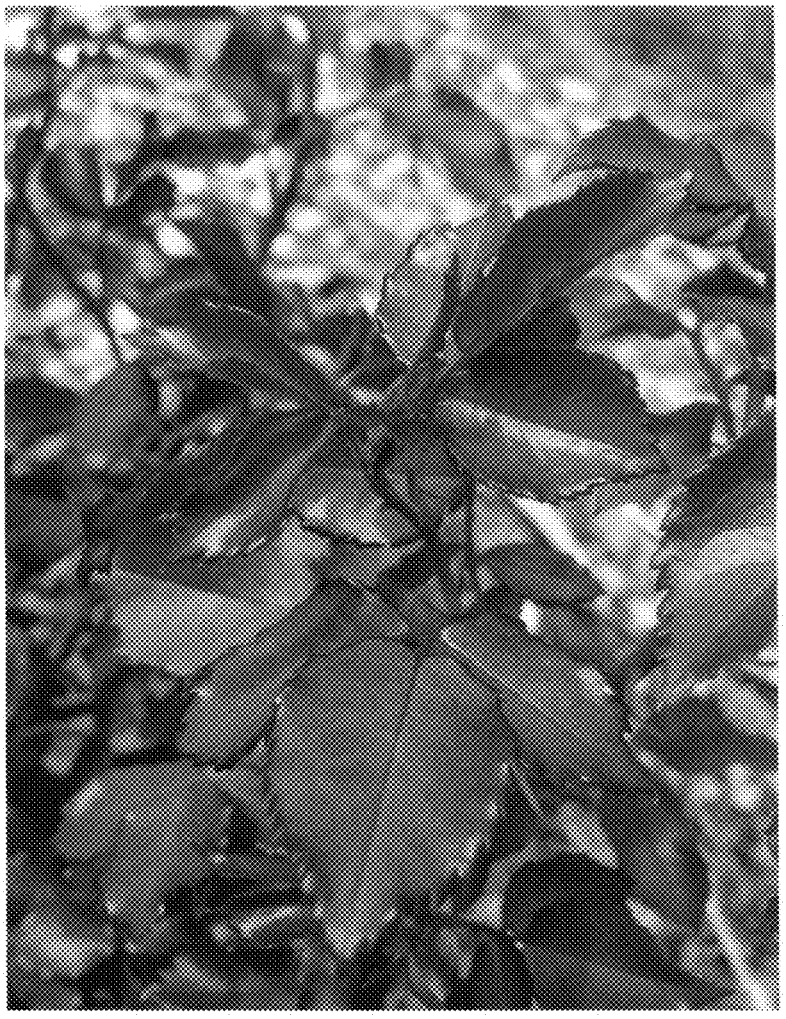
FIG. 6 illustrates the dark red coloration often temporarily produced on new growth when new growth is produced in full sun.
Figure 7:
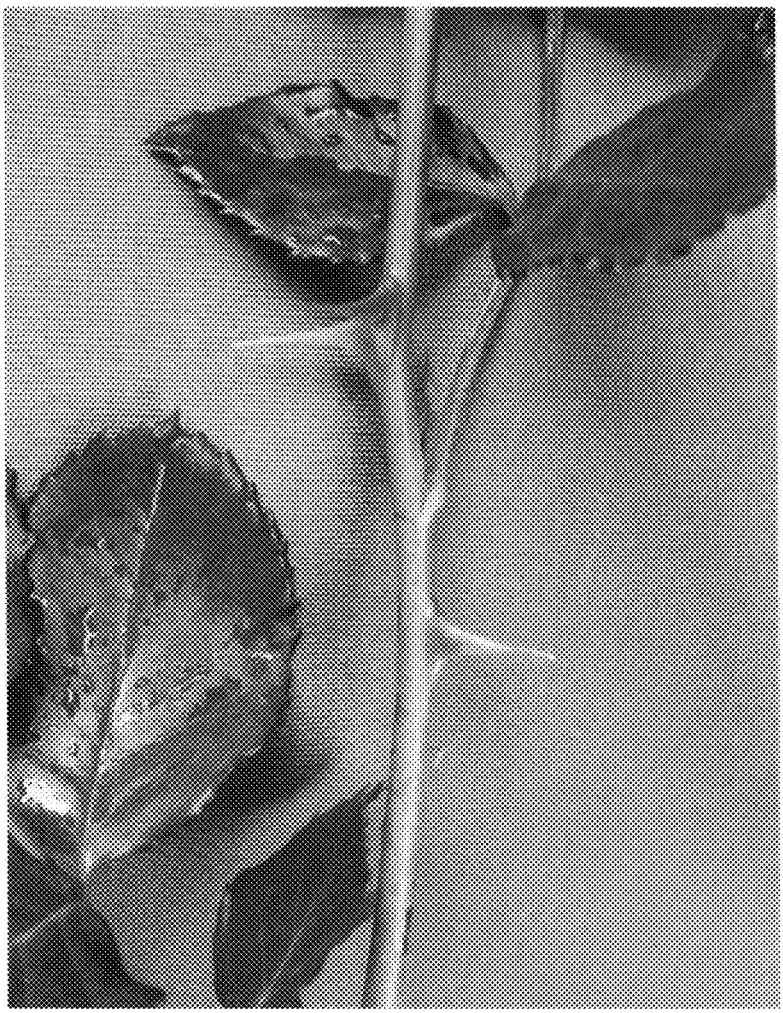
FIG. 7 illustrates a young stem with typical stem prickles.
Figure 8:
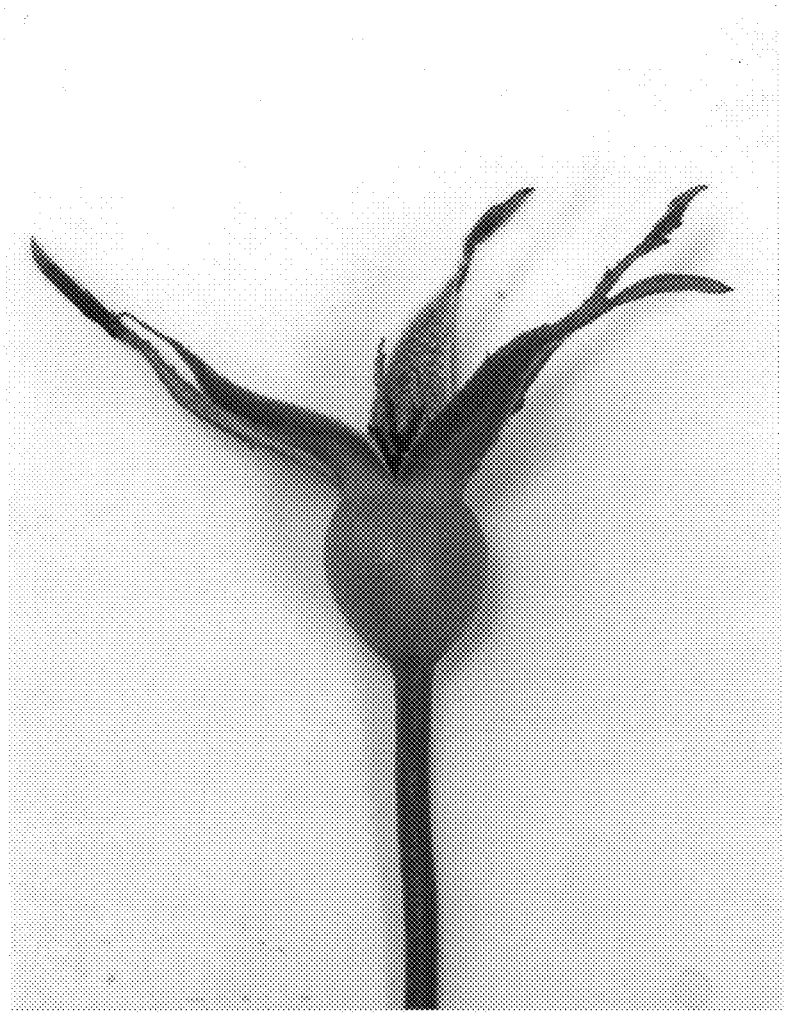
FIG. 8 illustrates a typical full-sized hip before it is fully ripe and the color turns orange.

The following is a detailed description of my new rose cultivar with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. Descriptions are based on observations of plants approximately six years of age that were propagated from semi-hardwood cuttings and growing in Edina, Minn.

Parentage:

*Seed parent*.—'Rise 'N Shine' (disclosed in U.S. Plant Pat. No. 4,231), a member of the miniature commercial class of roses.

*Pollen parent*.—'BAIine' (disclosed in U.S. Plant Pat. No. 16,659), a member of the shrub commercial class of roses.

Classification:

*Botanical*.—*Rosa hybrida*.

*Commercial*.—Shrub.

Flower:

*Blooming habit*.—Continuous.

Flower bud:

*Size*.—30-35 mm long and 18-22 mm in diameter when the petals start to unfurl.

*Form*.—The bud form is pointed.

*Color*.—When sepals first divide, visible petal color is Yellow Group 9B. When half blown, the upper or adaxial sides of the petals are Yellow Group 6C on the distal end and Yellow Group 9A at the proximal end. There is typically a soft peach overlay of color over the yellow petals on the adaxial side of the petals close in color to Orange Group 29C. This overlay disappears relatively quickly in the sunlight. This overlay subtly draws attention to and showcases the unfurling petals in the middle of the bloom. The lower or abaxial sides of the petals are Yellow Group 5C at the distal end and Yellow Group 9A at the proximal end.

*Sepals*.—Color: Green Group 143C on the abaxial side and Green Group 139D on the adaxial side. Length: 30-45 mm. Width: 6-8 mm. Shape: ovate to lanceolate with acuminate tips. Surface texture: Adaxial, Hoary. Abaxial, Generally smooth with sometimes some very small glandular hairs (<2 mm). There are three lightly appendaged sepals. There are two unappendaged sepals which have hoary edges.

*Receptacle*.—Color: Green Group 143B. Shape: proximal end is rounded and sides are relatively straight maintaining a consistent width before attachment to the sepals. Size: Medium, about 7 mm wide and 7 mm long. Surface: glabrous.

*Peduncle*.—Length: Medium, averaging about 30-40 mm. Surface: glabrous. Color: Yellow-Green Group 144A. Strength: Stiff, primarily erect.

Bloom:

*Size*.—Medium. Typical open diameter is 60-80 mm.

*Borne*.—Typically blooms are displayed one per stem.

*Stems*.—Strength: Strong. Length: Typically 20-50 cm. Stem diameter: Varies and is typically 4-6 mm. Larger stems arising from the base of the plant are about 1.0-1.3 cm in diameter, while smaller stems arising from secondary or tertiary stems within the plant canopy are typically 4-6 mm in diameter. Stem branching: Stems coming from the base of the plant terminate in a primary flower and then nodes along the stem typically break to produce stems that terminate in secondary flowers. These stems range in length and typically secondary flowers are produced at a similar plane as the primary bloom. This branching and flowering habit leads to a very full looking plant with flowers displayed densely around the perimeter of the shrub. Many of the secondary stems are of suitable length to serve as desirable cut flowers. Additional branches form from axillary buds from secondary stems to produce even more flowers.

*Form*.—When blooms first open: High centered (petals in the center of the flower are comparable in length to the petals around the perimeter of the flowers) petals unfurl in a symmetrical manner. This petal configuration and unfluring is commonly called exhibition form by rose growers and exhibitors. When blooms fully open: Petals are slightly undulating with reflexed margins. Center petals are generally oriented upright and outer petals are generally oriented horizontally leading to petals being spread out from one another and giving the open flowers a three dimensional hemispherical appearance.

*Permanence*.—Blooms retain their form to the end and petals generally cleanly abscise before turning brown.

*Petalage*.—Double blooms with petals and petaloids typically totaling 18-30.

*Color*.—The adaxial sides of the petals of half open blooms are primarily Yellow Group 6C throughout most of the petal and Yellow Group 9A at the base or proximal end of the petal. The color of the abaxial side of the petals is primarily Yellow Group 5C at the distal end and Yellow Group 9A at the proximal end.

*Discoloration*.—The petals fade to a cream color within about three to four days of opening. The color typically at this time on the adaxial side of the petal is Yellow Group 13D on the distal end of the petal and Yellow Group 5B on the proximal end of the petal. On the abaxial side of the petals the color is Yellow Group 13D on the distal end and Yellow Group 9B on the proximal end. At approximately day seven, just before the petals cleanly abscise, the color on both sides of the petal typically is Orange-White Group 159B at the distal end and Orange-White Group 159D at the proximal end.

*Fragrance*.—Slight to moderate. Character of fragrance: Fruity to spicy.

Petals:

*Texture*.—Thick and satiny to the touch.

*Length*.—3.0-4.0 cm.

*Width*.—The outermost petals of the bloom tend to be the widest petals and are typically 3.0-3.5 cm and the innermost petaloids are more narrow and are typically 1.5 cm.

*Shape*.—The outermost petals are generally orbicular and the shape of the petaloids towards the center of the flower are obovate to oblong.

*Margin*.—Entire.

*Apex shape*.—Mucronate for the outer petals and acute to rounded for the petaloids towards the center of the bloom.

*Base shape*.—Obtuse to acute.

*Arrangement*.—Multiple rows of overlapping petals.

*Petaloids*.—Most rose species, including commercial roses, have five true petals and all additional petal-like appendages are botanically petaloids. Petaloids are stamens or in some cases also pistils that develop into petal-like structures. Petaloids are often called petals in common vernacular in United States Plant Patents and the popular press. 'Gaye Hammond', like typical roses, has five true petals, frequently has between 18-25 petaloids that look like a typical petal, and often 1-3 petaloids that have some visible stamen development typically seen as a single anther along one of the edges. The petaloids with anthers attached are found at the transition area in the bloom between the most petal-like petaloids and the stamens. Pistils in 'Gaye Hammond' do not develop into petaloids. The size and color of the attached anthers on petaloids for 'Gaye Hammond' varies, but typically is the same as what is described later for anthers. Additionally, the color of the petal-like portion of the petaloid is typical for the color of a true petal or a more petal-like petaloid without visible anther development.

*Persistence*.—Petals drop off cleanly before drying.

*Lastingness*.—On the plant: Long (about 7-9 days). As a cut flower: Moderate (about 7 days).

Reproductive parts:

*Stamens*.—Number per flower: 50-75. Anthers — Size: Length before dehiscence: 2.5 mm, Width before dehiscence: 2.0 mm. Length after dehiscence: 1.5 mm. Width after dehiscence: 1.0 mm. Color: Before dehiscence: Yellow Orange Group 17B. After dehiscence: Orange Group 26B. Arrangement: Regular around styles. Filaments — Size: Length: 4-8 mm. Width: 0.25 mm. Color: Yellow-Orange Group 17C. Pollen — Color: Yellow Orange Group 17B.

*Pistils*.—Number per flower: 15-25. Styles — Color: Red Group 51B. Length: 6-7 mm. Stigmas — Color: Yellow Group 2C. Length: 1 mm. Ovary — Color of immature ovary: Green-White Group 157C. Length: 2-3 mm.

*Hips*.—The fleshy portion of rose hips, is hypanthium tissue and inside that tissue are achenes — individual single seeded fruits with a hard paricarp surrounding the embryo. Hips are common on 'Gaye Hammond'. Sepals persist and are present upon ripening. Hypanthium: Color immature: Green Group 146D. Color mature: Orange Group N25C. Shape: Generally obovate. Size: 18-23 mm long and 16-18 mm wide.

*Achenes* (*ripe*).—Color: Yellow Green Group 150D. Shape: Irregular and generally as wide as they are long. Size: 5-7 mm. Typically there are 1-6 achenes per hip.

Plant:

*Form*.—Rounded and upright growing shrub.

*Growth*.—Very vigorous, well-branched, and dense.

*Age at maturity*.—3 years.

*Mature plant*.—Height is 150 cm and width is 140 cm.

Leaf:

*Form*.—Leaves have three to seven leaflets with five leaflets being most common.

*Arrangement*.—Leaves are alternately arranged on stems.

*Size*.—Medium (12.0 cm long and 8.5 cm wide).

*Quantity*.—Normal.

*Leaflet color*.—New foliage: Adaxial side: Yellow-Green Group 146A Abaxial side: Yellow Green Group 146B. If new foliage is produced in full sunlight there is typically dark red highlights (Greyed-Purple Group 183C) that are more intense on the perimeter of leaflets compared to the center. These highlights fade as the leaves expand to their mature size. Old foliage: Adaxial side: Green Group 137A. Abaxial side: Yellow-Green Group 146B.

*Leaflet venation pattern*.—Pinnate reticulate.

*Leaflet venation color*.—The color of the veins is the same or very close to that of the overall leaf blade. New foliage: Adaxial side: Yellow-Green Group 146A Abaxial side: Yellow Green Group 146B. Old foliage: Adaxial side: Green Group 137A. Abaxial side: Yellow-Green Group 146C.

*Leaflet size*.—Terminal leaflets: Medium (5.0-6.0 cm long and 3.0-4.0 cm wide). Non-terminal leaflets: Medium (4.0-5.0 cm long and 2.5-3.5 cm wide).

*Leaflet shape*.—Ovate.

*Leaflet base shape*.—Obtuse.

*Leaflet apex shape*.—Acute to slightly acuminate.

*Leaflet texture*.—Very glossy, rugose. On the adaxial side of leaflets the veins are slightly recessed and on the abaxial side they are slightly elevated relative to the general leaf blade.

*Leaflet edge*.—Serrated with small single serrations.

*Petiole*.—Color. — Yellow-Green Group 146C.

*Petiole rachis*.—Color. — Yellow-Green Group 146C.

*Petiole underside*.—Generally smooth with small prickles. Prickles typically are Yellow-Green Group 146C and are 1-3 mm in length.

*Stipules*.—Short (about 1.0-1.3 cm in length). Color: Yellow-Green Group 146A, edges are generally entire or upon very close inspection there are sometimes very small serrations (less than 0.5 mm).

*Disease resistance*.—Very resistant to powdery mildew, black spot, and rust under observed growing conditions.

*Pest persistence*.—Not observed.

Wood:

*New wood*.—Color: Generally Yellow-Green Group 144A. Bark: Smooth.

*Old wood*.—Color: Yellow-Green Group 146C. Bark: Smooth.

Typical stem prickles:

*Quantity*.—Typical to slightly less than average. There are about 2 prickles between nodes towards the base of stems and 0-1 prickle between nodes closer to the flowers.

*Form*.—Straight sided and lanceolate in shape angled perpendicular to the stem to slightly downward.

*Length*.—10-15 mm.

*Width*.—Widened as they are attached to the stem (0.5-1.4 cm) and quickly narrowing to about 0.3 cm in width about 0.4 cm away from the stem. The rest of the prickle is lanceolate in shape and gently angles down to a sharp tip.

*Color when young*.—Yellow-Green Group N144D. If new prickles are produced in full sunlight there are typically dark red highlights (Greyed-Purple Group 183C) that are more intense on the proximal end of the pricles. These highlights fade as the prickles expand to their mature size.

*Color when mature*.—Greyed-Orange Group 165A.

Small, secondary stem prickles:

*Quantity*.—None.

Cytology:

*Ploidy*.—Tetraploid (2n=4x=28). Meristematic root tip cells in the stage of metaphase of mitosis were observed to have 28 chromosomes under a light microscope at 400× magnification.

Winter hardiness: Consistently crown hardy to United States Department of Agriculture cold hardiness zone 4.

I claim:

1. A new and distinct variety of rose plant of the shrub class, substantially as herein shown and described, characterized particularly by its upright, well-branched, and generally rounded plant habit; very vigorous growth; double flowers typically borne one per short to medium length stem; petal color starts out yellow with peach highlights and matures to creamy-white; continuous flowering throughout the growing season; strong resistance to black spot and powdery mildew; very glossy medium to dark green foliage; prominent relatively straight prickles and ability to root and grow vigorously from softwood and semi-hardwood cuttings.

* * * * *